United States Patent [19]

Steeg et al.

[11] Patent Number: 5,049,662
[45] Date of Patent: Sep. 17, 1991

[54] KIT FOR DIAGNOSING CANCER METASTATIC POTENTIAL

[75] Inventors: Patricia S. Steeg, Ellicott City; Lance A. Liotta, Potomac; Mark E. Sobel; Generoso Bevilacqua, both of Bethesda, all of Md.

[73] Assignee: The United States of America as represented by the Department of Health and Human Services, Washington, D.C.

[21] Appl. No.: 107,098

[22] Filed: Oct. 13, 1987

[51] Int. Cl.$^5$ .................... C07H 15/12; C07H 17/00; C12Q 1/68

[52] U.S. Cl. .......................... 536/27; 435/6; 536/28; 536/29; 436/811; 436/813

[58] Field of Search ................. 435/6; 536/27, 28, 29; 935/77, 78; 436/811, 813

[56] References Cited

FOREIGN PATENT DOCUMENTS 8603226 6/1986 World Int. Prop. O. .............. 435/6

Primary Examiner—Amelia Burgess Yarbrough
Assistant Examiner—Mindy B. Fleisher
Attorney, Agent, or Firm—Mishrilal Jain

[57] ABSTRACT

A new NM23 gene and its relationship with metastatic potential of tumor cells is described.

4 Claims, 4 Drawing Sheets

FIG.1
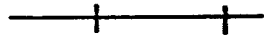
NM23
NM23-1
Hinf I  Rsa I  Cfo I                Pst I           Pst I
              Cfo I
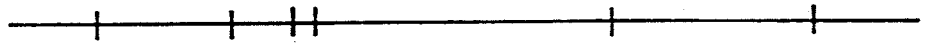
EcoRI        EcoRI + HhaI
Clone 16  Clone 19  M2  TK  TK-EVE    Clone 16  Clone 19  M2  TK  TK-EVE
FIG.2

FIG.3
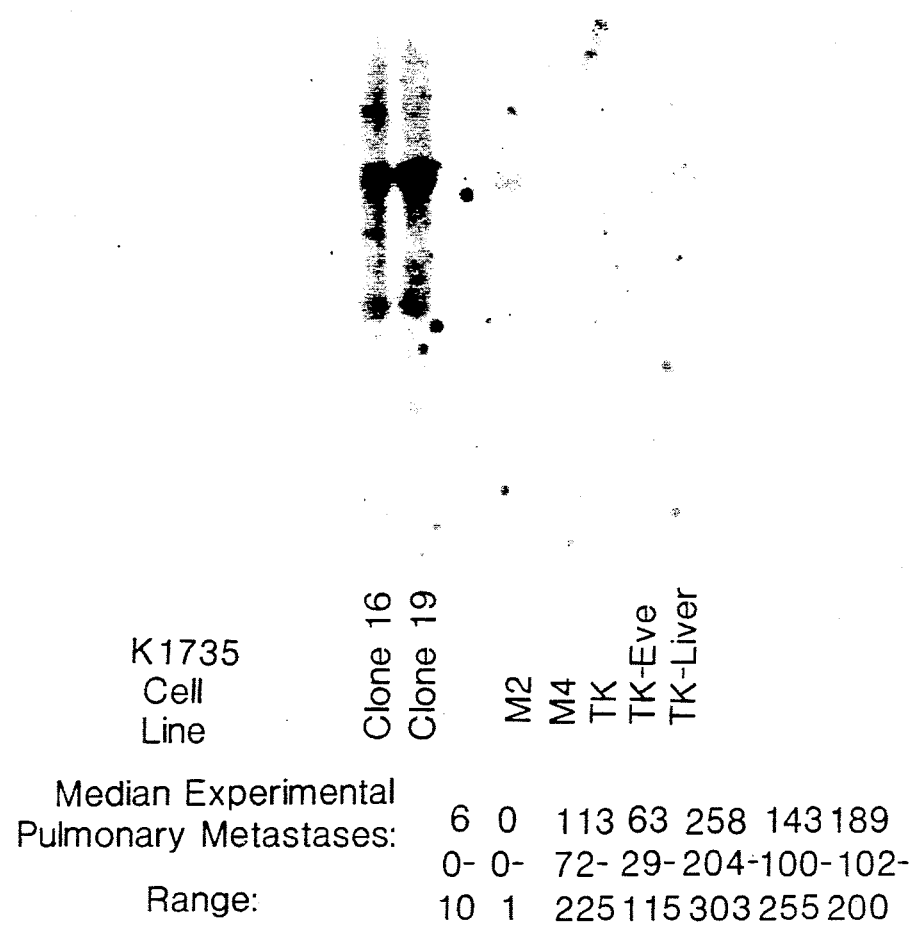
K1735 Cell Line: Clone 16, Clone 19, M2, M4, TK, TK-Eve, TK-Liver
Median Experimental Pulmonary Metastases: 6  0  113  63  258  143  189
Range: 0–10, 0–1, 72–225, 29–115, 204–303, 100–255, 102–200
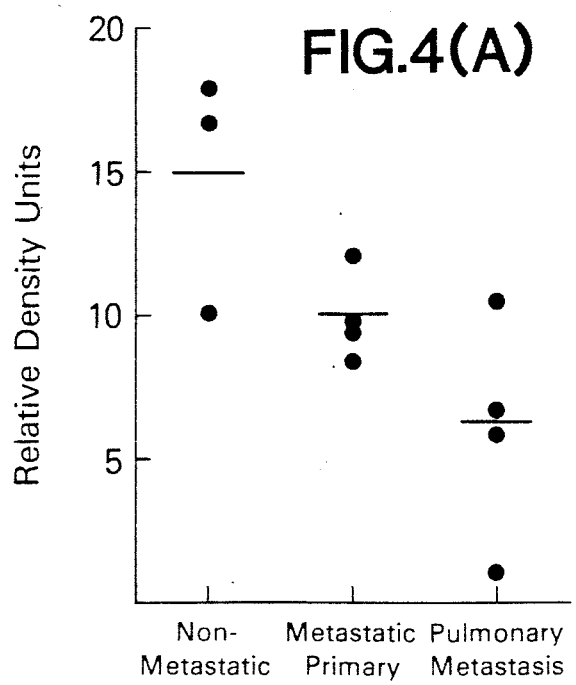
FIG.4(A)
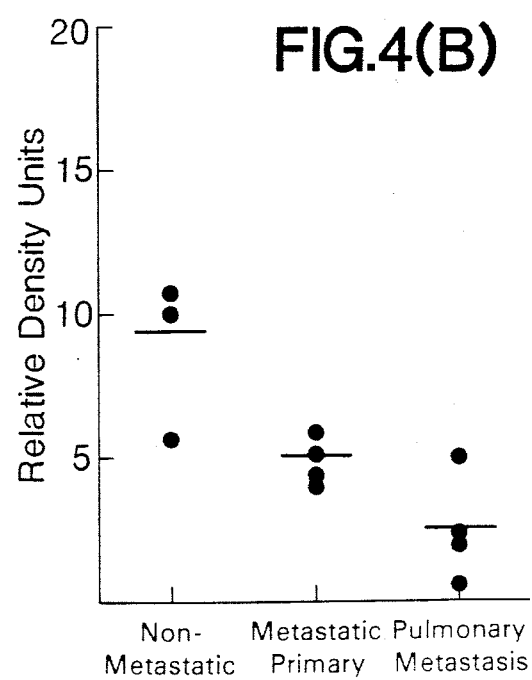
FIG.4(B)

| Cell Line: | RE4 | RE6 | RE2 | Ren 2 | 5R | 4R |
|---|---|---|---|---|---|---|
| c-Ha-*ras* | + | + | + | + | + | + |
| Ad2-E1a | + | + | + | − | − | − |

BALB/cf. RIII
BALB/cf. C3H

KIT FOR DIAGNOSING CANCER METASTATIC POTENTIAL

BACKGROUND OF THE INVENTION

1. Technical Field

The present invention is related generally to the field of diagnostic techniques for predicting cancer metastasis. More particularly, the present invention is related to providing a recombinant cDNA clone encoding NM23 gene whose expression is correlated with the metastatic potential of cancerous tumor cells.

2. State of the Art

Metastasis, the migration of tumor cells from the primary mass to other parts of the body, resulting in colonization of distant sites, remains a primary cause of death for patients with solid tumors. During the surgical/pathological intervention or diagnosis of neoplasia, tumor tissue samples are typically obtained or removed by biopsy. There is no genetic method, similar to the diagnostic kit of the present invention, presently available to predict the ability of cells from the tumor to metastasize.

SUMMARY OF THE INVENTION

It is, therefore, an object of the present invention to provide a cloned cDNA encoding the NM23 gene.

It is a further object of the present invention to provide an in vitro diagnostic kit for predicting the cancer metastatic potential of tumor cells.

Other objects and advantages of the present invention will become evident from the Detailed Description of the Invention.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 1 shows the restriction maps of pNM23 (NM23 in Figure) and pNM23-1. The cDNA inserts of pNM23 and pNM23-1 (NM23-1 in Figure) were isolated and restricted with the enzymes indicated, and the restriction digests electrophoresed in acrylamide gels. Band sizes were determined by comparisons to the mobility of known DNA markers;

FIG. 2 shows the Southern blot of K1735 murine melanoma cell lines' chromosomal DNA hybridized to the pNM23. cDNA insert. Chromos DNA was digested with EcoRI (left panel) and EcoRI+HhaI (right panel) and hybridized to the Bam HI-Pst I restriction fragment of the pNM23-1 cDNA clone;

FIG. 3 shows the Northern blot of K1735 murine melanoma cell lines' RNA hybridized to the pNM23 cDNA insert. Total cellular RNA was extracted from each K1735 cell line, electrophoresed on a 1% agarose gel containing formaldehyde, transferred to a nitrocellulose blot and hybridized to the $^{32}$P-labelled Pst I fragment of pNM23. Experimental metastatic potential was determined by i.v. injection of $10^4$ viable cells of each cell line into the tail vein of groups of 6-7 NIH nude mice. Gross pulmonary lung metastases were counted 3 weeks post-injection;

FIG. 4 shows the densitometric analysis of NM23 RNA levels of nitrosomethylurea (NMU)-induced rat mammary carcinomas of varying metastatic potentials. Mammary carcinomas were induced by a single injection of NMU into Buffalo rats; primary tumors and lung metastases were surgically removed, quick frozen, and total cellular RNA extracted. 10 µg (FIG. 4A) and 2 µg (FIG. 4B) of each RNA was appended to a slot blot, which was hybridized to $^{32}$P-labelled BamHI-Pst I restriction fragment of the pNM23-1 cDNA insert. The NM23 RNA content indicated on autoradiographs of the slot blot were quantitated by densitometry;

FIG. 5 shows the Northern blot analysis of NM23 RNA levels of Murine Mammary Tumor Virus (MMTV)-induced mouse mammary tumors of varying metastatic potentials. Total cellular RNA was extracted from mammary tumors of Balb/cf.RIII and Balb/cf.C3H mice which carry the indicated sources of MMTV. The mammary tumors of Balb/cf.RIII mice are of low metastatic potential, in contrast to the tumors of Balb/cf.C3H mice, which are of high metastatic potential. Ten µg of total cellular RNA was electrophoresed and transferred to a Northern blot, and hybridized to the $^{32}$P-labelled BamHI-Pst I restriction fragment of the pNM23-1 cDNA insert;

FIG. 6 shows the Northern blot analysis of NM23 RNA levels of transfected rat embryo fibroblast cell lines of varying metastatic potentials. Rat embryo fibroblasts were transfected with ras. resulting in highly metastatic cells (4R, 5R, Ren 2). Alternatively, rat embryo fibroblasts were cotransfected with ras, and the adenovirus Ela gene, resulting in cells of low metastatic potential (RE2, RE4, RE6). Total cellular RNA was extracted and Northern blots performed as described for FIG. 5;

DETAILED DESCRIPTION OF THE INVENTION

Figures 7, 8:
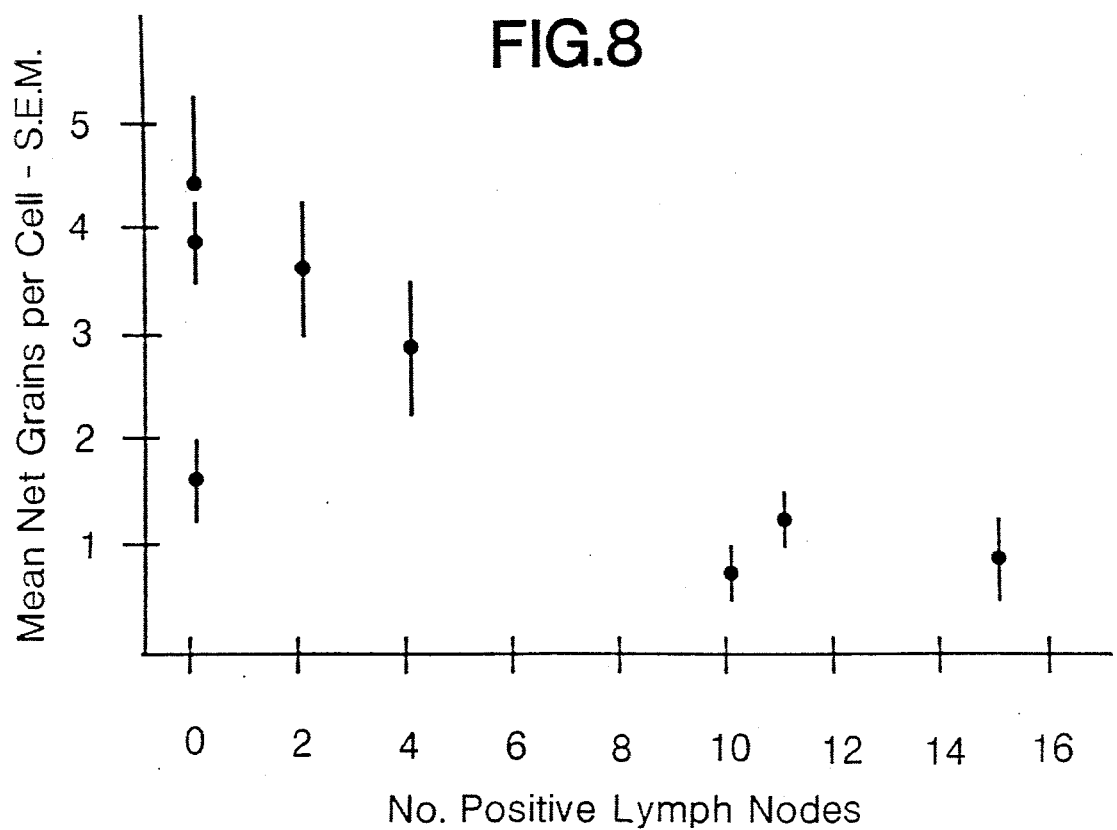
FIG. 7 shows in situ hybridization of the pNM23 cDNA insert to transfected rat embryo fibroblast cells of varying metastatic potentials. Cells from the RE6 (low metastatic) and 5R (high metastatic) lines (see FIG. 6) were centrifuged onto microscope slides and hybridized to $^{35}$S-labelled Pst I insert of pNM23. The hybridized slides were incubated for six days with photographic emulsion, developed, and stained with hematoxylin.
FIG. 8 shows in situ hybridization of the pNM23 cDNA insert to human breast carcinomas. Breast carcinomas from routine surgery were fixed and sectioned by standard histological methods, and hybridized in situ to $^{35}$S-labelled Pst I insert by pNM23 as described in FIG. 7. The number of grains/cell was determined in 50 cells of each section, and corrected for nonspecific background hybridization.

The above and various other objects and advantages of the present invention are achieved by providing a cDNA clone of NM23 gene characterized by the DNA sequence shown in Table 1. Below the DNA sequence is the predicted peptide sequence of NM23 protein.

TABLE 1

| GTC | GCA | GCC | GGC | GGT | AAA | GCC | TTG | TCA | TCT |
|---|---|---|---|---|---|---|---|---|---|
| GAA | GGG | GAC | CAT | GGC | CAA | CAG | TGA | GCG | TAC |
| CTT | CAT | TGC | CAT | CAA | GCC | TGA | TTC | AAG | GAG |

TABLE 1-continued

| CAC | TAC | ACT | GAC | CTG | AAG | GAC | CGC | CCC | TTC | 120 |
|-----|-----|-----|-----|-----|-----|-----|-----|-----|-----|-----|
| TTT | ACT | GGC | CTG | GTG | AAA | TAC | ATG met | CAC his | TCA ser | |
| GGA gly | CCA pro | GTG val | GTT val | GCT ala | ATG met | GTC val | TGG trp | GAG glu | GGT gly | 180 |
| CTG leu | AAT asn | GTG val | GTG val | AAG lys | ACA thr | GGC gly | CGC arg | GTG val | ATG met | |
| CTT leu | GGA gly | GAG glu | ACC thr | AAC asn | CCC pro | GCA ala | GAC asp | TCT ser | AAG lys | 240 |
| CCT pro | GGG gly | ACC thr | ATA ile | CGA arg | GGA gly | GAC asp | TTC phe | TGC cys | ATT ile | |
| CAA gln | GTT val | GGC gly | AGG arg | AAC asn | ATC ile | ATT ile | CAT his | GGC gly | AGC ser | 300 |
| GAT asp | TCT ser | GTA val | AAG lys | AGC ser | GCA ala | GAG glu | AAG lys | GAG glu | ATC ile | |
| AGC ser | TTG leu | TGG trp | TTT phe | CAG gln | CCT pro | GAG glu | GAG glu | CTG leu | GTG val | 360 |
| GAG glu | TAC tyr | AAG lys | AGC ser | TGT cys | GCG ala | CAG gln | AAC asn | TGG tyr | ATC ile | |
| TAT tyr | GAG glu | TGA | TAG | GAC | GGT | GCC | GGT | TTT | CTA | 420 |
| CCT | GCT | TAC | TCT | TGT | TCT | CAC | AGG | CAG | GGG | |
| ACC | AGC | AAC | CCT | AGA | TAT | TTC | TGG | AAC | TTC | 480 |
| TTT | GAC | CTG | GAA | GGA | ACC | TTT | GGG | AGC | CGT | |
| GAC | TCC | CTG | TGC | AGT | GTT | ACG | TGC | CAC | TGT | 540 |
| TAG | ATT | AAA | GTG | TTT | AAT | CTG | T | POLY A | | |

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

MATERIALS AND METHODS

Identification and Structural Form of the NM23 Gene

A murine cDNA clone for the NM23 gene was identified by differential screening of a murine melanoma cDNA library. Total cellular RNA was extracted from the K1735 murine melanoma TK-Eve cell line obtained as reported in Chemical and Experimental Metasasis (1987) and poly A-containing sequences isolated. Double-stranded cDNA was prepared from this RNA and was inserted into the Pst I site pBR322 plasmid by G/C tailing. RRI bacteria were transformed with the recombinant plasmids to generate a 40,000 component cDNA library. All techniques employed were those which are standard in the art to which this invention belongs and are well known to one of ordinary skill in the art. The recombinant plasmid thus obtained was designated pNM23.

The pNM23 cDNA clone was selected on the basis of differential hybridization of RNAs from low and high metastatic cell lines. Duplicate filters of the cDNA library were prepared: One set of filters was hybridized to $^{32}$P-labelled poly A+ RNA from the K1735 murine melanoma TK-Eve cell line, which is highly metastatic; the duplicate set of filters was hybridized to $^{32}$P-labelled RNA from the K1735 murine melanoma Clone 19 cell line, which is of low metastatic potential. Clones exhibiting differential hybridization to these two probes were tested for their pattern of hybridization to RNAs from seven K1735 murine melanoma cell lines of varying metastatic potentials. In these experiments, the cDNA inserts were purified, radiolabelled, and hybridized to Northern blots containing RNA from seven K1735 cell lines. The hybridization pattern of the pNM23 cDNA clone to each of the K1735 RNAs was inversely correlated with their experimental and spontaneous metastatic potentials.

The pNM32 cDNA clone contains a 250 bp insert; its restriction map is shown in FIG. 1. The DNA sequence was determined by using standard dideoxy and Maxam-Gilbert methods. The cDNA insert was radiolabelled and used to screen a murine fibroblast cDNA library to obtain a longer cDNA clone and its restriction map and DNA sequence are shown in FIG. 1 and Table 1. Computer analysis of the 3' 600 bp of this clone against Genebank animal, bacterial and viral sequences indicates that the NM23 is a novel, heretofore uncharacterized gene.

The murine NM23 gene is present as one band of EcoRI digested murine chromosomal DNA, each approximately 6 kb in length, on Southern blots (FIG. 2).

A deposit of NM23 has been made at the ATCC, Rockville, Md. on 10/7/87 under the accession number 67539. The deposits shall be viably maintained, replacing if it became non-viable, for a period of 30 years from the date of the deposit, or for 5 years from the last date of request for a sample of the deposit, whichever is longer, and made available to the public without restriction in accordance with the provisions of the law. The Commissioner of Patents and Trademarks, upon request, shall have access to the deposit.

Utility of the NM23 Gene

Hybridization of the cDNA clone for the NM23 gene to cellular RNA has predicted metastatic potential in both animal experimental metastasis model systems and human cancer. In each case, NM23 RNA levels were greatest in cells and tumors of low metastatic potential, and declined in highly metastatic specimens. NM23 expression is not related to immunologic phenotype.

Four animal experimental metastasis model systems have been employed. In the K1735 mouse melanoma system, seven cell lines derived from a single K1735 melanoma are available. The metastatic potential of these cell lines was determined by both i.v. injection of cells into the tail vein of mice (experimental metastasis) and s.c. inoculation of cells (spontaneous metastasis). The experimental metastatic potentials of the K1735 cell lines, shown in FIG. 3, are significantly different; spontaneous metastatic potential paralleled experimental metastatic potential. Five $\mu$g of total cellular RNA was electrophoresed in a formaldehyde containing agarose gel and transferred to a Northern blot; the blot was hybridized to $^{32}$P-nick translated cDNA insert from the pNM23 cDNA clone (FIG. 3). NM23 RNA levels are approximately ten fold higher in the two low metastatic K1735 cell lines (Clone 16 and Clone 19) than in five related highly metastatic K1735 cell lines (M2, M4, TK, TK-Eve and TK-Liver).

Hybridization data in a rat nitrosomethylurea (NMU) induced-mammary carcinoma model system provided further evidence of the diagnostic potential of NM23 gene. A single injection of NMU in Buffalo rats induced mammary carcinomas, 90% of which are nonmetastatic for periods of up to one year; NMU-induced metastatic carcinomas remain metastatic upon passage. Total cellular RNA was extracted from three types of NMU tumors: nonmetastatic mammary carcinomas, metastatic mammary carcinomas, and pulmonary metastases. RNA was applied to a slot blot and hybridized to the cDNA insert of the pNM23 cDNA clone (FIG. 4). Average NM23 RNA levels were found to be highest in nonmetastatic NMU tumors, i.e., 170% higher than metastatic mammary carcinomas and 320% higher than in pulmonary metastases. Variability observed in NM23 RNA levels within each type of tumor may reflect quantitative differences in metastatic potential which exist within a qualitative grouping.

Hybridization of the cDNA clone for the NM23 gene was also tested in murine mammary tumors of varying metastatic potentials. Balb/c mice carrying either the RIII or C3H strains of mouse mammary tumor virus (MMTV) develop mammary tumors which are of low and high metastatic potential, respectively. Total cellular RNA was extracted from mammary tumors in Balb/cf.RIIII and balb/cf.C3H mice, and NM23 RNA levels determined by Northern blot analysis using the BamHI-Pst I restriction fragment of pNM23-1 as a probe (FIG. 5). NM23 RNA levels were 3.5 fold greater in low metastatic balb/cf.RIII mammary tumors than in high metastatic Balb/cf.C3H tumors.

Rat embryo fibroblasts (REF) have been transfected with either ras or ras+adenovirus Ela genes; the ras transfected cells have significantly greater experimental metastatic potential than ras+Ela transfected cells. Average NM23 RNA levels of ras+Ela transfected REF are three-fold greater than those of ras transfected cells (FIG. 6). These data were confirmed by in situ hybridization of the pNM23 cDNA insert to ras or ras+Ela transfected cells: average cellular RNA in ras+Ela REF were significantly higher than in ras REF (FIG. 7).

In summary, NM23 RNA levels were higher in less metastatic cells and tumors than in highly metastatic specimens in four animal metastases model systems. An advantage of the animal experiments is the availability of closely related specimens that differ in very few parameters, one of which is metastatic potential. Differential hybridization of pNM23 cDNA clones has been demonstrated both in vitro and in vivo, and to several types of cancers employing different methods to confirm the data.

NM23 RNA levels were also found to be differentially expressed in human cancer tissues. In the study shown in FIG. 8, NM23 RNA levels in breast carcinoma surgical specimens were determined by in situ hybridization. Human primary breast cancer (infiltrating ductal carcinoma) samples were obtained at mastectomy including axillary lymph node dissection. The level of NM23 RNA expression in a given tumor was compared to the number of axillary lymph nodes positive for metastases in that same patient. As shown, significant differences in the hybridization intensity of the pNM23 cDNA insert were observed. Comparison of NM23 levels and traditional indicators of metastatic potential indicate the diagnostic potential of this gene: a correlation coefficient of $-0.8$ was obtained between the number of positive axillary lymph nodes and NM23 RNA levels. NM23 levels have also been found to be differentially expressed in human colon carcinomas (data not shown).

It is clear from the results presented herein that NM23 gene or a portion thereof can be employed for hybridization with tumor RNA to determine the tumor NM23 RNA levels and thus predict metastatic potential.

The NM23 gene can be produced in volumes suitable for commercial use by inserting it into any suitable expression vector, such as viral phages, bacterial plasmids, and the like. Either chromosomal or cDNA fragments of the NM23 gene, from any species can be inserted into a vector. The recombinant vector is then grown in large quantity, and the NM23 insert isolated by a variety of methods well known to one of ordinary skill in the art. The NM23 DNA can be used in the native state or in a labelled form (i.e.. radiolabelled, biotinylated or the like) in the diagnostic assays.

Tumor NM23 RNA levels can be determined by any suitable method, two examples of which are illustrated: (1) For in situ hybridization, tumors can be fixed and sectioned by standard techniques and the NM23 probe hybridized to a tumor section. NM23 RNA levels can be determined on a cell-by-cell basis in this assay. This technique affords the advantages of determining cellular heterogeneity of NM23 RNA levels, which may have diagnostic value. Also, this method precludes artifactual NM23 RNA levels of surrounding normal cells and invading lymphocytes. (2) Gross tumor NM23 content can also be determined. For this purpose, RNA is extracted from a portion of the tumor, and immobilized on to a filter. The filter is then hybridized to the NM23 probe, and NM23 RNA levels determined. This procedure offers the advantages of rapid results and ease of preparation and quantitation.

Prediction of metastatic potential from NM23 RNA levels comprises comparison of tumor NM23 levels with reference standards for the tumor type under consideration. Optimally, reference standard RNA levels is determined as side-by-side controls in the NM23 assay to control day-to-day variations of techniques and reagents. The quantitation of NM23 RNA levels and comparison to standards can be performed either by lab personnel or by automated systems.

The diagnostic kit comprises at least a container containing NM23 gene, either in whole (for example, 750, bp long) or in part (for example, 250 bp fragment) or inserted into a vector. The gene could be made available either in a lyophilized or a buffered medium. For longer shelf-life, the contents of the container could be cryopreserved. The kit may also include instructions for performing the assay to determine NM23 levels in a cell or tissue sample.

It is clear, of course, that given the nucleotide sequence of NM23, the same is readily synthesized by commercially available synthesizer equipments and such synthesized product then used in accordance with the present invention.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. Isolated, synthetic NM23 gene.
2. The gene of claim 1 cloned in a cloning vector.
3. The gene of claim 2 having the identifying characteristics of ATCC 67539.
4. NM23 gene having been recovered from the clone of claim 3.

* * * * *